US005600000A

United States Patent [19]

King

[11] Patent Number: 5,600,000
[45] Date of Patent: Feb. 4, 1997

[54] REDUCTIVE AMINATION PROCESSES FOR THE SELECTIVE PRODUCTION OF AMINO-ETHYLETHANOLAMINE

[75] Inventor: Stephen W. King, Scott Depot, W. Va.

[73] Assignee: Union Carbide Chemicals & Plastics Technology Corporation, Danbury, Conn.

[21] Appl. No.: 461,549

[22] Filed: Jun. 5, 1995

Related U.S. Application Data

[63] Continuation of Ser. No. 171,539, Dec. 22, 1993, abandoned.

[51] Int. Cl.$^6$ .................................................. C07C 209/02
[52] U.S. Cl. .......................................... 564/480; 564/479
[58] Field of Search .................................. 564/480, 479, 564/478

[56] References Cited

U.S. PATENT DOCUMENTS

| | | | |
|---|---|---|---|
| 4,123,462 | 10/1978 | Best | 260/585 B |
| 4,977,266 | 12/1990 | Burgess et al. | 564/398 |
| 5,068,329 | 11/1991 | Burgess et al. | 544/402 |
| 5,202,490 | 4/1993 | Burgess et al. | 564/480 |
| 5,352,835 | 10/1994 | Dai et al. | 564/480 |

OTHER PUBLICATIONS

Rose et al. (eds.) The Condensed Chemical Dictionary, 6th Ed. (1961), p. 21.

*Primary Examiner*—Brian M. Burn
*Attorney, Agent, or Firm*—J. B. Mauro

[57] ABSTRACT

The present invention relates to improved reductive amination processes whereby monoethanolamine and ammonia are reacted in the presence of hydrogen and various reductive amination catalysts to yield high selectivity to acyclic products such as aminoethylethanol-amine, while reducing the production of cyclic products such as piperazine. When the process of the present invention is carried out in the presence of reductive amination catalyst containing metals such as nickel or nickel-rhenium on transitional alumina carriers, productivity and selectivity to the desired products is increased. Alternatively, the process may be carried out in the presence of hydrotalcite-like or takovite-like catalysts which have been enhanced by the use of promoters to achieve the desired results.

5 Claims, No Drawings

1

REDUCTIVE AMINATION PROCESSES FOR THE SELECTIVE PRODUCTION OF AMINO-ETHYLETHANOLAMINE

This application is a Continuation of prior U.S. application Ser. No. 08/171,539 Filing Date Dec. 22, 1993 (now abandoned).

BACKGROUND OF THE INVENTION

The present invention relates to reductive amination processes useful in the selective production of aminoethylethanolamine (AEEA). More specifically, the invention provides catalysts, which when used with specific promoters in the reductive amination of monoethanolamine (MEA) and ammonia, produce a product composition having higher levels of aminoethylethanolamine and reduced levels of cyclics such as piperazine (PIP).

AEEA is typically considered a by-product of processes used in the preparation of ethylenediamine (EDA). A significant portion of EDA made commercially is by the continuous reaction of monoethanolamine (MEA) and ammonia in the presence of hydrogen over a fixed bed reductive amination catalyst. The reaction generates a variety of polyalkylene polyamines as well. Illustrative of many of them are the following:

AEEA-N-(2-aminoethyl)ethanolamine

PIP-Piperazine

HEP-N-(2-hydroxyethyl)piperazine

AEP-N-(2-aminoethyl)piperazine

DETA-Diethylenetriamine

TETA-Triethylenetetramine

TEPA-Tetraethylenepentamine

PEHA-Pentaethylenehexamine

Until recently, AEEA was viewed as an unwanted by-product and a precursor to PIP (see U.S. Pat. Nos. 2,479,657 and 3,383,417). The value of AEEA has risen considerably in recent years because significant commercial uses have evolved for it. Because most commercial processes have been designed to produce EDA and minimize the formation of PIP, owing to the limited demand for PIP, little is known about the manipulation of the commercial reductive amination processes to generate larger amounts of AEEA. There are very few patents directed to the manufacture of AEEA, and most do not rely on the reaction of MEA and ammonia under reductive amination conditions.

The following patents are directed to reductive amination processes for producing alkyleneamines product mixtures, which may contain AEEA in the product mix.

U.S. Pat. No. 4,123,462 describes a nickel-rhenium reductive amination catalyst for the production of desirable alkylamines and reduction of undesirable by-products having improved selectivity and increased conversion. The nickel-rhenium catalyst comprises rhenium and nickel impregnated on a support material selected from the group consisting of aluminas, silicas, silica-aluminas, kieselguhrs or diatomaceous earths and silica-titanias. The patent suggests that when selectivity is of primary concern, the amination process should not be run at high conversions, as it has been found that selectivity to the preferred aminoalkanes decreases as conversion increases. It is suggested that the formation of aminoethylethanolamine leads to increased piperazine formation at these higher conversions via intramolecular ring closure of AEEA.

U.S. Pat. No. 5,068,329 describes a continuously generated alkyleneamines producers composition rich in AEEA prepared by the reaction of MEA in the presence of a reductive amination catalyst. Ammonia is not used as a reactant. The product distribution shows the production of about 50% to about 90% AEEA, less than about 3% EDA, less than 2% DETA and about 5% to 18% cyclics including PIP, AEP and HEP. The patent lists numerous known reductive amination catalyst useful in the process including those which typically contain metals such as nickel, rhodium, rhenium, zinc, palladium, platinum and the like supported on various materials such as alumina, silica, silica-alumina, kieselguhr, diatomaceous earth and silica-titania.

The patent states that support materials are not equivalent in their ability to form active catalysts and that the actual effectiveness of a material as a support in a potentiated nickel catalyst is generally not predictable in advance. In addition, the nickel-rhenium catalyst disclosed can contain other metals in admixture with the nickel and rhenium which do not detrimentally affect the catalytic properties of the catalyst. It is stated that certain metals can extend the activity life and other physical properties of the Ni—Re catalysts, these metals include lanthanum, calcium, magnesium, strontium, lithium, potassium, barium, cesium, tungsten, iron, ruthenium, copper, silver, zinc, cobalt, uranium, titanium, boron and manganese.

U.S. Pat. No. 5,202,490 describes a process for the manufacture of an alkyleneamines reaction product mixture without a net increase in piperazine by the reaction of MEA and ammonia using a reductive amination catalyst. Again, the product mixture is characterized by the presence of about 15% to 35% DETA, about 10% to about 35% AEEA, about 15% to about 55% EDA (net generated) and about 3% to about 25% cyclics including PIP, AEP and HEP.

The patent describes the same catalysts enumerated above and in addition states that other preferred reduction amination catalysts are composed of rhenium, nickel and boron impregnated on a support material selected from the group consisting of alumina (e.g. alpha), silicas, silica-aluminas, kieselguhrs or diatomaceous earths and silica-titanias, wherein the ratio of nickel to boron to rhenium is in the range of from about 2:2:1 to about 30:30:1 and the total nickel, boron and rhenium present is in the range of about 3 to about 30 percent by weight of the support material.

The increased production of AEEA is achieved by using lower ammonia/MEA mole ratios to favor MEA self condensation. Such changes in reaction conditions may lead to harsher reaction conditions, e.g. higher pH, which may contribute to deactivation and degradation of the catalyst and catalyst supports, and produces larger amounts of undesired aminoalkyl ethanolamines.

It would be beneficial to have a process which increases the selective production of AEEA, without generating large amounts of cyclic alkylenepolyamine products.

SUMMARY OF THE INVENTION

According to the present invention, there are provided processes for the selective production of AEEA, which minimize PIP and other cyclic by-products. In one embodiment, the process may be carried out in the presence of reductive amination catalysts containing at least one catalytically effective reductive amination metal on transitional alumina carriers. In addition, catalyst promoters such as compounds containing elements selected from Group IA and IIA of the Periodic Table may be incorporated with the catalytically effective reductive amination metal to further enhance selectivity.

In another embodiment, the process may be carried out in the presence of reductive amination catalysts prepared from a group of materials known as hydrotalcite-like or takovite-like compositions having the following structure:

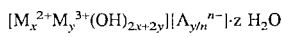

where $M_x^{2+}$ is either magnesium or nickel; $M_y^{3+}$ is aluminum; and A is carbonate providing a valence of $n^-$.

With hydrotalcite-like catalysts which are comprised of magnesium and aluminum, nickel or nickel/rhenium are incorporated with the hydrotalcite-like catalysts to yield catalysts which give high AEEA productivities with low piperazine production.

A preferred embodiment of the present invention comprises promoters, preferably zinc or magnesium, added to nickel/rhenium catalysts which have been incorporated with transitional alumina carriers.

DESCRIPTION OF THE PREFERRED EMBODIMENTS

It is an objective of this invention to effect a reaction of MEA in the presence of hydrogen and ammonia to selectively produce desired amounts of AEEA, without increasing the production of cyclic amines. Reductive amination processes are well known in the art. The processes are effected by feeding to a tubular reactor zone containing the catalyst, a feedstream of MEA, hydrogen and ammonia typically in a mole ratio of ammonia to MEA of about 1 to about 30; where hydrogen comprises about 10 to about 50 mole percent of the feed. Water may be provided in the feed up to 20 weight percent of the weight of the MEA. The reaction zone is defined as a zone in the reactor containing the catalyst where the reaction is initiated. The reaction zone ends when the principal reactions between MEA and ammonia ceases or the feed stream is out of contact with the catalyst, whichever is the later to occur in time.

In one embodiment, the reaction is carried out in the presence of reductive amination catalysts containing at least one catalytically effective reductive amination metal incorporated with transitional alumina carriers.

Transitional aluminas or activated aluminas are defined in Kirk-Othmer (Vol. 2, p. 291, 1992) as a series of partially hydroxylated aluminum oxide (excluding alpha aluminas which are anhydrous in nature). In general, as a hydrous alumina precursor is heated, hydroxyl groups are driven off leaving a porous solid structure. As the activation temperature increases through the transitional phases, the crystal structures become more ordered thus allowing for identification of the transitional aluminas by x-ray diffraction. The sequences of transition are affected not only by the starting materials but also by their coarseness of crystallinity, heating rates, and impurities. The following transitions are generally accepted as the transitions when the starting material is coarse gibbsite in air:

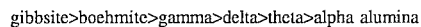

Of the transitional aluminas described above, the delta and theta phases are preferred carriers for the process of the invention. Other preferred transitional aluminas include mixtures of transitional aluminas such as gamma/theta, delta/theta, theta/alpha phases or mixtures thereof.

Transitional alumina carriers may be characterized using an X-ray Diffractometer by methods known in the art. The following table lists the accepted 2-theta values for the transitional aluminas as supplied by the Joint Committee on Powder Diffraction Standards -International Center for X-Ray Diffraction:

| Transitional Aluminas | | | | | | | |
|---|---|---|---|---|---|---|---|
| gamma | 19.58 | 31.94 | 37.60 | 39.49 | 45.79 | 60.76 | 66.76 |
| delta | 17.65 | 19.49 | 21.82 | 31.14 | 32.78 | 34.74 | 39.96 | 39.49 |
| | 45.55 | 46.54 | 47.57 | 50.67 | 60.03 | 61.35 | 62.26 | 64.18 |
| | 66.76 | 67.31 | 73.33 | 75.37 | | | | |
| theta | 15.5 | 16.25 | 19.54 | 31.509 | 32.778 | 34.939 | 36.743 | 38.871 |
| | 39.911 | 44.856 | 46.4242 | 47.5849 | 50.6803 | 51.3931 | 52.6308 | 54.5575 |
| | 56.7218 | 58.7033 | 61.2553 | 62.3387 | 64.0501 | 65.3714 | 67.4008 | |
| alpha | 25.5 | 35.4 | 38.0 | 43.6 | 52.8 | 57.6 | 63.05 | 66.7 |
| | 68.4 | | | | | | | |
| Cat. F | 39.4672 | 45.7691 | 46.0159 | 46.4638 | 46.8969 | 65.8291 | 66.4935 | 67.2831 |
| Cat. I | 31.2119 | 32.7897 | 36.7688 | 39.5019 | 39.7188 | 44.8422 | 66.5872 | 67.3378 |
| Cat. J | 19.6 | 25.5362 | 31.2322 | 32.7675 | 35.1091 | 36.6600 | 37.7275 | 38.9028 |
| | 39.8125 | 43.3084 | 44.7931 | 47.5881 | 52.5094 | 57.4538 | 66.4734 | 67.3944 |
| | 68.1550 | | | | | | | |
| Cat. L | 25.5075 | 35.0803 | 37.7012 | 43.2813 | 52.4825 | 57.4247 | 66.4453 | 68.1325 |

Although the crystallinity of alpha alumina is highly distinctive when compared to the transitional aluminas, in mixed phases which contain small amounts of alpha alumina, the amount of alpha alumina present is not easily quantified. However, due to the extremely low surface areas of alpha aluminas, useful mixed phases containing alpha alumina can be determined by those which fall within the surface area ranges described below.

Transitional aluminas are typically considered to be intermediate surface area carriers. The surface areas are preferably between about 10 $m^2/gm$ and about 200 $m^2/gm$; more preferably between about 40 $m^2/gm$ and about 180 $m^2/gm$; and most preferably between about 80 $m^2/gm$ and about 140 $m^2/gm$.

The transitional aluminas used in making the catalyst may be of any convenient shape or size. The shape of the support usually will depend upon the shape required in the particular apparatus used to perform the reductive amination. Catalysts can be made on the transitional alumina carriers in the form of powders, spherical pellets, extruded strips and the like. Impregnated spherical pellets ranging in diameter from about 0.3 cm to about 0.5 cm and extruded strips of a cylindrical-type shape ranging from about 0.8 mm to about 1.3 cm in length are typical of those which can be used as carriers.

The particular method of incorporating the transitional alumina carriers with nickel and rhenium is insignificant to the final activity or selectivity of the final catalyst in amination processes; however, impregnated catalysts generally perform better than precipitated catalysts. The amount of metals provided on the transitional alumina carriers can affect or vary the catalytic activity or selectivity.

One technique for impregnating the nickel and rhenium onto the carrier is by incipient wetness techniques using aqueous solutions of salts of the metals. Various organic and inorganic salts may be used in impregnation solutions. The following description will be limited to nickel, nickel and rhenium, or nickel, rhenium and boron salts. However, it is to be fully understood that the invention is not limited to the use of these metals and that other metals, typically used on reductive amination catalysts, may also be used in combination with the preferred transitional alumina carriers to obtain improved results. These metals include, for example, copper, cobalt, chromium, rhodium, iridium, ruthenium, zinc, palladium, platinum and the like.

Examples of suitable nickel-containing salts are nickel hexahydrate, nickel formate and nickel acetate tetrahydrate and the like. Typical rhenium salts employed include ammonium perrhenate and perrhenic acid.

In preparing the salt solutions, the amount of total metal desired to be impregnated on a specific quantity of transitional alumina carrier and the relative atom ratio of nickel to rhenium should be considered, as both factors have been found to affect the final properties of the catalysts.

Some active catalysts have been found to be those in which the nickel to rhenium atom ratio is between 1:1 and 30:1. In most previous patents, the maximum activity has been shown to occur with this ratio being between about 5:1 and 20:1. However, it has been unexpectedly found that by using the transitional alumina carriers of the present invention, that the levels of rhenium can be significantly lowered while still maintaining high activity and selectivity. For example, in the present invention, the desired atom ratio of nickel to rhenium is typically in the range of from about 1:1 to about 200:1; more preferably from about 5:1 to about 100:1; and most preferably from about 10:1 to about 50:1. Although there may be some decrease in selectivity at the higher ratios, these catalysts containing lower levels of rhenium are still active catalysts.

The total metals to be impregnated onto the transitional alumina carriers also has an effect on the activity of the catalyst. The total nickel and rhenium metal content is preferably in the range of about 1% to 30% by weight of the carrier; more preferably from about 5% to 15%.

Where relatively large amounts of metal are to be impregnated on carriers, a single impregnation step may not be sufficient. Although an impregnation solution may be prepared with minimum amount of solvent required to dissolve the metal salts, the total amount of the impregnation solution may be greater than that which the carrier can absorb. In such case, a portion of the impregnation solution less than the maximum absorption amount is used to initially contact the carrier. After contacting, the carrier is dried and then contacted with an additional amount of impregnation solution. The sequential steps of contacting with solution and drying are continued until all of the impregnation solution is used. A typical drying step can comprise heating the impregnated carrier to a temperature of 120° C. for several hours. Evacuation drying may also be used, where the carrier is cooled under reduced pressure, or the material may be calcined at elevated temperatures (>300° C.) to decompose the salt to the metal oxide.

It may also be advantageous to dry the transitional alumina carriers prior to impregnation in order to ensure that the carriers will take up as much of the solution as possible. This pre-drying step also enables the metal to permeate more deeply into the carrier during impregnation. The penetration of the metal into the carrier may be further increased by techniques known to those skilled in the art such as by increasing the time the carrier is in contact with the solution. Other impregnation techniques are well known in the art and may be utilized in the present invention.

After the transitional alumina carrier is impregnated with the desired amount of nickel and rhenium, it is completely dried and then activated by a reduction step. The drying step to be used is any technique which sufficiently evaporates the volatile constituents of the impregnating solution. The drying step may comprise heating the catalyst to a temperature of about 120° C. under inert atmospheres such as in the presence of nitrogen, followed by cooling under reduced pressure.

The catalyst may then be activated, preferably by contacting the catalyst with a hydrogen atmosphere at an elevated temperature of from about 200° C. to about 600° C. for periods of from about 45 minutes to about 4 hours. The reduced catalyst is best handled in the absence of air in order to maintain optimal performance and prevent pyrophoric behavior. The catalyst may be stabilized by gentle oxidation, carbon dioxide treatment, or other conventional techniques for stabilizing pyrophoric catalysts, and may then be handled in air prior to its utilization. The catalyst is then activated in a separate step or in situ. The specific conditions for reduction are dependent upon the particular catalyst composition being activated, as is known in the art.

Prior to the activation step, the catalyst may be optionally calcined. In a preferred calcining step, the catalyst is heated to temperatures in the range of about 300° C. to 550° C. for one minute to about 3 hours or more. It is preferred that the calcining step be carried out in air. The drying step referred to above may be replaced by the calcining step or activating step.

The amount of Ni—Re catalyst present in the process of the invention depends on many variables including the relative proportions of the reactants, reaction conditions and degree of conversion and selectivity desired. Moreover, the amount of catalyst will depend also on the nature of the catalyst itself, e.g., its metal loading and activity and age. The catalyst must be present in the reaction zone in sufficient catalytic amount to enable the desired reaction to occur.

Preferred reductive amination catalysts are catalyst composed of nickel, nickel and rhenium or nickel, rhenium and boron, impregnated on transitional alumina carriers, preferably on a delta or theta phase transitional alumina, including mixed phases such as gamma/theta, delta/theta, theta/alpha phases or mixtures thereof; wherein the ratio of nickel to rhenium is in the range of from about 10:1 to about 50:1; and the total amount of nickel and rhenium present is in the range of from about 5 to about 15 percent by weight of the transitional alumina carrier. When boron is present as an additional component, typical atom ratios of nickel to boron are from about 0.1 to about 6.0.

The selectivity of these catalysts may be enhanced by the use of promoters. As used herein, a promoter for the catalyst is defined as any metal (or oxide) which when incorporated into the catalyst gives enhanced AEEA productivity and/or a higher AEEA/PIP selectivity. The preferred metals or oxides for use as promoters are compounds containing elements selected from Group IA, Group IIA and Group IIB of the Periodic Table, especially magnesium, zinc, calcium, potassium and mixtures thereof. The promoters may be added to the nickel:rhenium catalysts on transitional aluminas either by co-impregnation with nickel and rhenium or by adding to the carrier prior to incorporation of the nickel and rhenium salts. Preferred promoter levels for the nickel:rhenium catalysts on transitional aluminas range from about 0.1 to 5.0 percent by weight of the carrier, and is dependent on the nickel:rhenium present in the catalyst. For example, the amount of promoter should not exceed the amount of nickel present on a weight/weight percent basis.

Another preferred group of catalysts useful in the reductive amination processes of the present invention includes materials having the formula:

$$[M_x^{2+}M_y^{3+}(OH)_{2x+2y}][A_{y/n}^{n-}]\cdot z\ H_2O$$

where $M_x^{2+}$ is either magnesium or nickel; $M_y^{3+}$ is aluminum; A is carbonate providing a valence of n-, wherein n is at least 1 (e.g. between 1 and 4 and most often between 1 and 3) and z is a positive number.

Included in the materials identified above are those based on exchangeable anion clay minerals. For example, where M is magnesium and Q is aluminum, these compounds are related to hydrotalcites (hydrotalciteolike), while compositions in which M is nickel and A is aluminum are related to takovites (takovite-like). In fact, mixed metal oxides prepared using magnesium, and nickel as the divalent cation and aluminum as the trivalent cation exhibit the typical X-ray diffraction pattern of a hydrotalcite.

The above described hydrotalcite-like or takovite-like compositions are further prepared by heating at a temperature in the range of 200° C. to 800° C. for a period of time of about 12 to 24 hours under an inert atmosphere such as nitrogen or in appropriate cases under an oxidizing atmosphere such as air.

Calcination of the hydrotalcite-like or takovite-like compositions dehydrates the composition and converts, at least partially, the metal hydroxides to metal oxides.

Certain compositions falling within the above formula, such as hydrotalcite, which comprises a magnesium-aluminum hydroxide carbonate, and takovite, which comprises a nickel-aluminum hydroxide carbonate, are naturally occurring compositions. However, such compounds, as well as their related compositions, also can be prepared synthetically from inexpensive starting materials using well-known coprecipitation techniques. Procedures for direct synthesis of such materials are described in Itaya et al., *Inorg. Chem.* (1987) 6:624–626; Taylor, R. M., *Clay Minerals* (1984) 19:591–603; Reichle, U.S. Pat. No. 4,476,324; Bish, D. L. *Bull. Mineral* (1980), 103:170–175 and Miyata et al., *Clays and Clay Minerals* (1977) 25:14–18. Using direct synthesis one has the ability to vary within wide limits the $M^{2+}$ and $M^{3+}$ atomic ratio as well as the anion.

The hydrotalcite-like compositions in which $M^{2+}$ is Mg and $M^{3+}$ is aluminum are inactive for use as reductive amination catalysts until nickel is incorporated. In a typical preparation, nickel and rhenium salts are dissolved in ammonium hydroxide and added to the hydrotalcite-like catalysts. The impregnation may be done in sequential steps with calcination in air at 340° C. between each step. The material is then reduced as described below.

Takovite-like catalysts, which already contain nickel, may be reduced and used without further metal oxide impregnation. Alternatively, nickel promoters such as rhenium may be used to increase the activity of these takovite-like catalyst compositions.

The process of the invention is not limited to a confining set of conditions. The feed stream may be liquid, supercritical fluid or gaseous, and the reaction product stream taken from the reaction zone may be liquid, supercritical fluid or gaseous. It is not necessary that the feed stream and the reaction product stream be in the same physical state.

The reactor design is also not narrowly critical. The feed thereto may be upflowing or downflowing, and design features in the reactor which optimize plug flow in the reactor may be employed.

The reactants may be fed as a stream, typically continuously, to the bed of the catalyst. The catalyst is usually a fixed bed of solid particles (pellets, tablets, extrudates, spheres, etc.) which comprise the catalyst deposited on the preferred transitional alumina carriers, as described above. The reaction occurs in the bed and thus the bed defines the reaction zone. The effluent from the bed or the reaction zone is also a stream comprising the unreacted components of the feed stream and the principal reaction products EDA, DETA and AEEA, plus a number of other amine compounds.

The conditions for reaction are also not narrowly limited. For example, the pressures for carrying out the process may range from about 1000 psig to about 3000 psig, more preferably from about 1200 psig to about 2200 psig. In addition, the process may typically be carried out at temperatures from about 120° C. to about 300° C., preferably from about 140° C. to about 200° C.

The following examples are intended for the purpose of illustrating this invention and not for the purpose of limiting it. In order to make direct comparisons of the various catalysts evaluated, a specific set of reaction conditions was chosen. As is well known in the art, the product mixtures of any reaction process can be changed by varying such things as the feed mole ratio of reactants, product recycle, hydrogen concentration, feed space velocity, time on organics, temperature and the like. The selection of these operating variables is dependent on the desired conversions and product selectivity.

EXAMPLES

In the examples set forth in the tables below, the catalyst of choice is placed in a tubular reactor having an outside diameter of about 2.54 cm and an overall length of about 76 cm. The catalyst portion of the reactor comprised a length of about 61 cm, capable of accommodating about 150 cubic centimeters of catalyst. The reactor is made of 316 stainless steel.

For each of the examples, the tubular reaction system is brought to the designated conditions. The ammonia and MEA are premixed to the appropriate feed mole ratio and then pressure fed to the system. The liquid feed is then mixed with hydrogen and this mixture is passed to a preheater prior to entering the reaction zone.

The reaction mixture is passed through the reaction zone in a downflow fashion. The pressure in the reaction zone is controlled by a motor valve at the outlet of the reactor. After leaving the reaction zone, the pressure of the stream is reduced from that of the reaction zone to slightly above atmospheric. This stream is then passed through a trap where the hydrogen is separated from the condensables which are collected in a semi-batch fashion. The condensable sample, which contains unreacted ammonia and MEA and the products of the reaction, is then analyzed for water by a Karl-Fisher procedure and for organics (amines) by capillary gas chromatography.

Catalysts are generally prepared by using incipient wetness techniques with multiple impregnations, and calcinations in air after each impregnation step. The doped carrier is then reduced in a Lindberg furnace equipped with an Iveron Pacific Model 2300A programmable setpoint controller at a temperature of 340° C. over a period of about 5 hours. The catalysts are activated at 180° C. overnight under hydrogen after charging to the reactor described above. A 10:1 molar ratio of ammonia:MEA, is then feed to the reactor as the liquid feed in the presence of hydrogen.

The catalysts and/or carriers employed in the examples hereinafter were obtained from Norton Company, Akron, Ohio and United Catalysts, Inc. The following materials were purchased and used in preparing the catalysts, without further purification: nickel nitrate hexahydrate (Fisher), nickel formate (Strem), ammonium hydroxide (Baker), ammonium perrhenate (Strem), orthoboric acid (Johnson Matthey, formerly Alfa), magnesium acetate tetrahydrate (Baker), potassium nitrate (Baker), and zinc carbonate hydroxide monohydrate (Aldrich). Distilled water was used in all aqueous solutions.

Certain of the catalysts and/or carriers were treated as follows:

| Catalyst | Catalyst Preparation |
| --- | --- |
| A | Ni:Al Takovite (2:1), calcined at 425° C. |
| B | 1.75 grams of ammonium perrhenate was dissolved in 41 ml of water and added to 55 grams of a Ni:Al Takovite (2:1) and calcined at 340° C., using sequential steps of impregnation with calcination between each step. |
| C | 0.85 grams of ammonium perrhenate was dissolved in 41 ml of water and added to 55 grams of a Ni:Al Takovite (2:1) and calcined at 340° C., using sequential steps of impregnation with calcination between each step. |
| D | 14.8 grams of nickel formate and 1.70 grams of ammonium perrhenate were dissolved in 28 ml of ammonium hydroxide, and added to 55 grams of magnesium oxide (Alfa), calcined in air at 340° C. for about 1 hr., using sequential steps of impregnation with calcination between each step. |
| E | 14.06 grams of nickel formate and 1.68 grams of ammonium perrhenate were dissolved in 100 ml of ammonium hydroxide, and added to 55 grams of Mg:Al hydrotalcite (2:1), calcined in air at 340° C. for about 1 hr., using sequential steps of impregnation with calcination between each step. |
| F | 22.1 grams of nickel nitrate hexahydrate, 1.7 grams of ammonium perrhenate and 5.2 grams of boric acid were dissolved in 45 ml of water and added to 55 grams of UCIT-869 silica-alumina (95:2.5) having a surface area of 68 m2/gm; using sequential steps of impregnation with calcination at 340° C. between each step. |
| G | 22.1 grams of nickel nitrate hexahydrate, 1.7 grams of ammonium perrhenate and 38.3 grams of magnesium nitrate were dissolved in 75 ml of water and added to 55 grams of Norton SN 74707, a gamma/theta-alumina having a surface area of 100 m2/gm; using sequential steps of impregnation with calcination at 340° C. between each step. |

-continued

| Catalyst | Catalyst Preparation |
| --- | --- |
| H | 15.4 grams of magnesium acetate tetrahydrate was dissolved in water and added to 55 grams of Norton SN-74707, a gamma/theta-alumina having a surface area of 100 m2/gm; the material was calcined in air at 340° C. for about 1 hr. prior to the addition of 14.15 grams of nickel formate, and 1.69 grams of ammonium perrhenate dissolved in 60 ml of ammonium hydroxide, applied in sequential steps with calcination between each step. |
| I | 14.16 grams of nickel formate and 1.70 grams of ammonium perrhenate were dissolved in 55 ml of ammonium hydroxide, and added to 55 grams of UCIT-869, a silica-alumina (95:2.5) having a surface area of 68 m2/gm; calcined in air at 340° C. for about 1 hr., using sequential steps of impregnation with calcination between each step. |
| J | 5.84 grams of magnesium acetate tetrahydrate was dissolved in water and added to 55 grams of T-869, a silica-alumina (95:2.5) having a surface area of 68 m2/gm; the material was calcined in air at 340° C. for about 1 hr. prior to the addition of 14.16 grams of nickel formate, and 1.69 grams of ammonium perrhenate dissolved in 55 ml of ammonium hydroxide, applied in sequential steps with calcination between each steps. |
| K | 4.07 grams of zinc basic carbonate (Aldrich) and 2.3 grams of ammonium carbonate were dissolved in ammonium hydroxide and added to 55 grams of T-869, a silica-alumina (95:2.5) having a surface area of 68 m2/gm; the material was calcined in air at 340° C. for about 1 hr. prior to the addition of 14.14 grams of nickel formate, and 1.72 grams of ammonium perrhenate dissolved in 60 ml of ammonium hydroxide, applied in sequential steps with calcination between each steps. |
| L | 4.08 grams of zinc basic carbonate (Aldrich) and 2.3 grams of ammonium carbonate were dissolved in ammonium hydroxide and added to 52.5 grams of Norton SN-74707, a gamma/theta-alumina having a surface area of 100 m2/gm; the material was calcined in air at 340° C. for about 1 hr. prior to the addition of 14.12 grams of nickel formate, and 1.72 grams of ammonium perrhenate dissolved in 50 ml of ammonium hydroxide, applied in sequential steps with calcination between each steps. |
| M | 0.53 grams of magnesium acetate tetrahydrate was dissolved in water and added to 55 grams of a gamma/theta alumina having a surface area of 80 m2/gm; the material was calcined in air at 340° C. for about 1 hr. prior to the addition of 14.04 grams of nickel formate, and 1.16 grams of ammonium perrhenate dissolved in 105 ml of ammonium hydroxide, applied in sequential steps with |

| Catalyst | Catalyst Preparation |
|---|---|
| N | calcination between each step. 2.22 grams of magnesium acetate tetrahydrate was dissolved in water and added to 55 grams of a gamma/theta alumina having a surface area of 80 m2/gm; the material was calcined in air at 340° C. for about 1 hr. prior to the addition of 22.17 grams of nickel nitrate hexahydrate, and 0.61 grams of ammonium perrhenate dissolved in 90 ml of water applied in sequential steps with calcination between each step. |
| O | 3.87 grams of magnesium acetate tetrahydrate was dissolved in water and added to 55 grams of a gamma/theta alumina having a surface area of 80 m2/gm; the material was calcined in air at 340° C. for about 1 hr. prior to the addition of 22.14 grams of nickel nitrate hexahydrate, and 0.88 grams of ammonium perrhenate dissolved in 86 ml of water, applied in sequential steps with calcination between each step. |
| P | 5.51 grams of magnesium acetate tetrahydrate was dissolved in water and added to 55 grams of a gamma/theta alumina having a surface area of 80 m2/gm; the material was calcined in air at 340° C. for about 1 hr. prior to the addition of 14.08 grams of nickel formate, and 0.35 grams of ammonium perrhenate dissolved in 107 ml of ammonium hydroxide, applied in sequential steps with calcination between each step. |
| Q | 0.21 grams of zinc acetate dihydrate was dissolved in water and added to 55 grams of a gamma/theta alumina having a surface area of 80 m2/gm; the material was calcined in air at 340° C. for about 1 hr. prior to the addition of 22.14 grams of nickel nitrate hexahydrate, and 0.35 grams of ammonium perrhenate dissolved in 90 ml of water, applied in sequential steps with calcination between each step. |
| R | 0.85 grams of zinc acetate dihydrate was dissolved in water and added to 55 grams of a gamma/theta alumina having a surface area of 80 m2/gm; the material was calcined in air at 340° C. for about 1 hr. prior to the addition of 14.05 grams of nickel formate, and 0.88 grams of ammonium perrhenate dissolved in 105 ml of ammonium hydroxide, applied in sequential steps with calcination between each step. |
| S | 1.48 grams of zinc acetate dihydrate was dissolved in water and added to 55 grams of a gamma/theta alumina having a surface area of 80 m2/gm; the material was calcined in air at 340° C. for about 1 hr. prior to the addition of 14.08 grams of nickel formate, and 0.62 grams of ammonium perrhenate dissolved in 105 ml of ammonium hydroxide, applied in sequential steps with calcination between each step. |
| T | 2.06 grams of zinc acetate dihydrate was dissolved in water and added to 55 grams of a gamma/theta alumina having a surface area of 80 m2/gm; the material was calcined in air at 340° C. for about 1 hr. prior to the addition of 22.14 grams of nickel nitrate hexahydrate, and 1.15 grams of ammonium perrhenate dissolved in 86 ml of water, applied in sequential steps with calcination between each step. |
| U | 1.63 grams of potassium nitrate tetrahydrate was dissolved in water and added to 55 grams of a gamma/theta alumina having a surface area of 80 m2/gm; the material was calcined in air at 400° C. for about 1 hr. prior to the addition of 22.16 grams of nickel nitrate hexahydrate, and 0.62 grams of ammonium perrhenate dissolved in 90 ml of water, applied in sequential steps with calcination between each step. |
| V | 22.13 grams of nickel nitrate hexahydrate, 1.71 grams of ammonium perrhenate, and 5.25 grams of orthoboric acid were dissolved in water and added to 55 grams of a gamma/theta alumina having a surface area of 80 m2/gm; using sequential steps with calcination at 340° C. between each step. |

The conditions used in the examples and the results are set forth in the following tables:

| Example No. | 1 | 2 | 3 | 4 | 5 | 6 |
|---|---|---|---|---|---|---|
| Process Parameters | | | | | | |
| Catalyst Type | A | A | A | B | B | B |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 8.31 | 8.36 | 8.88 | 8.43 | 12.86 | 12.09 |
| Ammonia/MEA mole ratio | 10.00 | 10.00 | 10.00 | 10.00 | 10.00 | 10.00 |
| Calculated Results | | | | | | |
| MEA conversion, % | 15.35 | 23.83 | 38.24 | 20.39 | 32.86 | 56.05 |
| EDA/PIP weight ratio | 27.72 | 15.32 | 8.25 | 13.35 | 14.79 | 4.95 |
| DETA/PIP weight ratio | 2.58 | 2.00 | 1.05 | 1.58 | 2.30 | 1.09 |
| AEEA/PIP weight ratio | 14.94 | 9.50 | 4.91 | 3.26 | 3.25 | 1.02 |

-continued

| Crude Product Composition, wt. % | | | | | | |
|---|---|---|---|---|---|---|
| EDA | 58.80 | 53.10 | 51.55 | 68.13 | 67.84 | 57.63 |
| PIP | 2.12 | 3.47 | 6.25 | 5.10 | 4.59 | 11.64 |
| DETA | 5.46 | 6.92 | 6.58 | 8.07 | 10.56 | 12.64 |
| AEEA | 31.70 | 32.91 | 30.66 | 16.63 | 14.89 | 11.82 |
| AEP | 0.91 | 0.91 | 0.90 | 0.92 | 0.59 | 1.20 |
| HEP | 0.24 | 0.49 | 1.08 | 0.22 | 0.17 | 0.51 |
| TETA | 0.37 | 0.67 | 0.74 | 0.70 | 0.89 | 1.93 |
| Others | 0.40 | 1.54 | 2.23 | 0.21 | 0.48 | 2.62 |

| Example No. | 7 | 8 | 9 | 10 | 11 | 12 |
|---|---|---|---|---|---|---|
| Process Parameters | | | | | | |
| Catalyst Type | C | C | C | D | D | D |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 12.50 | 12.09 | 10.96 | 11.80 | 11.60 | 11.54 |
| Ammonia/MEA mole ratio | 10.00 | 10.00 | 10.00 | 10.00 | 10.00 | 10.00 |
| Calculated Results | | | | | | |
| MEA conversion, % | 20.23 | 44.38 | 73.19 | 3.55 | 5.99 | 11.09 |
| EDA/PIP weight ratio | 42.46 | 2.54 | 3.06 | 53.24 | 65.04 | 36.87 |
| DETA/PIP weight ratio | 4.67 | 0.47 | 1.03 | 2.47 | 3.67 | 3.28 |
| AEEA/PIP weight ratio | 11.67 | 0.58 | 0.55 | 34.98 | 27.50 | 15.23 |
| Crude Product Composition, wt. % | | | | | | |
| EDA | 70.46 | 43.57 | 47.85 | 57.32 | 66.29 | 64.43 |
| PIP | 1.66 | 17.14 | 15.66 | 1.08 | 1.02 | 1.75 |
| DETA | 7.75 | 7.99 | 16.16 | 2.66 | 3.74 | 5.72 |
| AEEA | 19.37 | 10.00 | 8.62 | 37.66 | 28.03 | 26.62 |
| AEP | 0.28 | 7.44 | 2.74 | 1.25 | 0.91 | 0.77 |
| HEP | 0.00 | 0.69 | 0.81 | 0.00 | 0.00 | 0.00 |
| TETA | 0.48 | 0.96 | 4.23 | 0.00 | 0.00 | 0.00 |
| Others | 0.01 | 12.22 | 3.93 | 0.03 | 0.02 | 0.71 |

| Example No. | 13 | 14 | 15 |
|---|---|---|---|
| Process Parameters | | | |
| Catalyst Type | E | E | E |
| Catalyst Weight, gm. | 50 | 50 | 50 |
| Temperature, °C. | 160 | 170 | 180 |
| Pressure, psig | 1814 | 1814 | 1814 |
| MEA SV, gmol/hr/kgcat | 13.00 | 15.41 | 12.86 |
| Ammonia/MEA mole ratio | 10.00 | 10.00 | 10.00 |
| Calculated Results | | | |
| MEA conversion, % | 6.06 | 10.90 | 28.05 |
| EDA/PIP weight ratio | 74.18 | 51.11 | 15.27 |
| DETA/PIP weight ratio | 4.44 | 4.54 | 3.25 |
| AEEA/PIP weight ratio | 44.86 | 23.45 | 8.66 |
| Crude Product Composition, wt. % | | | |
| EDA | 59.60 | 63.54 | 51.75 |
| PIP | 0.80 | 1.24 | 3.39 |
| DETA | 3.57 | 5.64 | 11.02 |
| AEEA | 36.04 | 29.15 | 29.36 |
| AEP | 0.00 | 0.42 | 0.62 |
| HEP | 0.00 | 0.00 | 0.45 |
| TETA | 0.00 | 0.00 | 1.75 |
| Others | 0.00 | 0.01 | 1.67 |

The examples in Table I show the effectiveness of hydrotalcite-like and takovite-like materials. Catalyst A shows high selectivity to AEEA for a takovite-like material. Catalysts B and C show a rhenium promoter with takovite-like catalysts, which yields higher activity. Catalyst D shows magnesium oxide as an ineffective carrier for nickel:rhenium catalysts; whereas, catalyst E shows a similar nickel:rhenium catalyst on a hydrotalcite-like carrier as effective, giving both improved activity and selectivity to AEEA.

| Example No. | 16 | 17 | 18 | 29 | 20 | 21 |
|---|---|---|---|---|---|---|
| Process Parameters | | | | | | |
| Catalyst Type | F | F | F | G | G | G |

-continued

| | | | | | | |
|---|---|---|---|---|---|---|
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 8.04 | 8.52 | 8.90 | 10.59 | 10.46 | 11.25 |
| Ammonia/MEA mole ratio | 10.00 | 10.00 | 10.00 | 10.00 | 10.00 | 10.00 |
| Calculated Results | | | | | | |
| MEA conversion, % | 24.85 | 42.80 | 57.81 | 1.89 | 3.65 | 5.95 |
| EDA/PIP weight ratio | 9.20 | 4.56 | 2.42 | X | 83.32 | 50.86 |
| DETA/PIP weight ratio | 1.70 | 0.96 | 0.51 | X | 10.48 | 4.85 |
| AEEA/PIP weight ratio | 1.77 | 0.59 | 0.23 | X | 39.27 | 29.19 |
| Crude Product Composition, wt. % | | | | | | |
| EDA | 64.20 | 59.15 | 51.03 | 54.69 | 60.74 | 57.96 |
| PIP | 6.98 | 12.97 | 21.12 | 0.00 | 0.73 | 1.14 |
| DETA | 11.89 | 12.43 | 10.78 | 21.51 | 7.64 | 5.52 |
| AEEA | 12.38 | 7.62 | 4.91 | 22.10 | 28.63 | 33.27 |
| AEP | 1.36 | 2.65 | 4.96 | 1.70 | 1.19 | 0.91 |
| HEP | 0.28 | 0.49 | 0.75 | 0.00 | 0.00 | 0.48 |
| TETA | 2.06 | 2.30 | 2.06 | 0.00 | 0.00 | 0.00 |
| Others | 0.86 | 2.39 | 4.40 | 0.00 | 1.09 | 0.71 |

| Example No. | 22 | 23 | 24 | 25 | 26 | 27 |
|---|---|---|---|---|---|---|
| Process Parameters | | | | | | |
| Catalyst Type | H | H | H | I | I | I |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 10.90 | 11.06 | 9.30 | 10.22 | 11.60 | 11.37 |
| Ammonia/MEA mole ratio | 10.00 | 10.00 | 10.00 | 10.00 | 10.00 | 10.00 |
| Calculated Results | | | | | | |
| MEA conversion, % | 16.72 | 30.44 | 53.12 | 19.87 | 36.16 | 50.65 |
| EDA/PIP weight ratio | 7.95 | 7.93 | 3.53 | 14.49 | 7.69 | 4.39 |
| DETA/PIP weight ratio | 1.63 | 2.26 | 1.24 | 1.91 | 1.62 | 0.98 |
| AEEA/PIP weight ratio | 8.29 | 5.40 | 1.67 | 2.59 | 1.44 | 0.66 |
| Crude Product Composition, wt. % | | | | | | |
| EDA | 39.89 | 44.11 | 41.16 | 70.06 | 61.46 | 56.77 |
| PIP | 5.01 | 5.56 | 11.66 | 4.84 | 8.00 | 12.92 |
| DETA | 8.15 | 12.57 | 14.41 | 9.23 | 12.95 | 12.70 |
| AEEA | 41.59 | 30.03 | 19.48 | 12.52 | 11.49 | 8.57 |
| AEP | 0.92 | 0.85 | 2.08 | 1.65 | 2.10 | 3.41 |
| HEP | 0.26 | 0.33 | 0.73 | 0.24 | 0.42 | 0.70 |
| TETA | 1.80 | 3.37 | 5.11 | 0.77 | 1.95 | 2.16 |
| Others | 2.37 | 3.18 | 5.38 | 0.69 | 1.63 | 2.77 |

| Example No. | 28 | 29 | 30 | 31 | 32 | 33 |
|---|---|---|---|---|---|---|
| Process Parameters | | | | | | |
| Catalyst Type | J | J | J | K | K | K |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 15.08 | 14.11 | 13.84 | 10.98 | 11.34 | 11.29 |
| Ammonia/MEA mole ratio | 10.00 | 10.00 | 10.00 | 10.00 | 10.00 | 10.00 |
| Calculated Results | | | | | | |
| MEA conversion, % | 11.63 | 26.06 | 38.93 | 15.09 | 28.79 | 45.55 |
| EDA/PIP weight ratio | 27.50 | 10.00 | 5.28 | 12.06 | 7.38 | 4.05 |
| DETA/PIP weight ratio | 2.49 | 1.46 | 0.93 | 2.07 | 1.78 | 1.20 |
| AEEA/PIP weight ratio | 5.01 | 2.04 | 1.01 | 4.74 | 2.50 | 1.07 |
| Crude Product Composition, wt. % | | | | | | |
| EDA | 73.69 | 66.23 | 58.86 | 57.42 | 53.89 | 48.42 |
| PIP | 2.68 | 6.62 | 11.15 | 4.76 | 7.30 | 11.95 |
| DETA | 6.67 | 9.67 | 10.37 | 9.88 | 13.01 | 14.40 |
| AEEA | 13.43 | 13.49 | 11.27 | 22.56 | 18.26 | 12.74 |
| AEP | 0.58 | 1.48 | 3.38 | 1.85 | 1.90 | 3.11 |
| HEP | 0.52 | 0.58 | 1.06 | 0.22 | 0.36 | 0.64 |
| TETA | 0.50 | 1.06 | 1.44 | 1.55 | 2.78 | 4.07 |
| Others | 1.93 | 0.87 | 2.46 | 1.75 | 2.49 | 4.67 |

| Example No. | 34 | 35 | 36 |
|---|---|---|---|
| Process Parameters | | | |
| Catalyst Type | L | L | L |
| Catalyst Weight, gm. | 50 | 50 | 50 |
| Temperature, °C. | 160 | 170 | 180 |
| Pressure, psig | 1814 | 1814 | 1814 |
| MEA SV, gmol/hr/kgcat | 10.86 | 11.05 | 9.35 |
| Ammonia/MEA mole ratio | 10.00 | 10.00 | 10.00 |
| Calculated Results | | | |
| MEA conversion, % | 28.83 | 47.80 | 68.20 |
| EDA/PIP weight ratio | 4.54 | 3.69 | 1.77 |
| DETA/PIP weight ratio | 1.23 | 1.47 | 0.69 |
| AEEA/PIP weight ratio | 5.18 | 1.97 | 0.48 |
| Crude Product Composition, wt. % | | | |
| EDA | 34.18 | 38.74 | 36.42 |
| PIP | 7.53 | 10.51 | 20.54 |
| DETA | 9.24 | 15.43 | 14.26 |
| AEEA | 39.01 | 20.75 | 9.90 |
| AEP | 0.88 | 1.38 | 3.85 |
| HEP | 0.36 | 0.60 | 1.01 |
| TETA | 2.83 | 6.22 | 6.35 |
| Others | 5.97 | 6.37 | 7.67 |

The examples in Table II show comparisons between a preferred silica/alumina carrier (UCI T-869) of U.S. Pat. No. 4,123,462 and U.S. Pat. No. 5,068,329, and preferred gamma/theta alumina carriers of the present invention.

Catalyst F contains boron, a preferred promoter of U.S. Pat. Nos. 4,123,462 and 5,068,329. Catalyst I was prepared without a promoter, Catalyst J with a magnesium promoter, and Catalyst K with a zinc promoter. All of the above comparative examples are on the preferred silica/alumina carriers of the above cited patents.

The results show magnesium is detrimental to catalyst performance for silica/alumina carriers lowering both the catalytic activity and selectivity to AEEA, while zinc lowers the catalytic activity.

Catalysts G, H, and L were prepared on a preferred gamma/theta alumina carrier of the present invention. Catalyst G shows that high levels of magnesium (10 weight percent) are detrimental to catalyst performance (lower activity); however, at 5 weight percent, magnesium provides both high catalytic activity and selectivity to AEEA, when added to a nickel:rhenium catalyst on transitional alumina carriers. Catalyst L shows a similar effect when zinc (5 weight percent) is added as a promoter for the nickel:rhenium catalyst on a preferred gamma/theta alumina carrier.

| Example No. | 37 | 38 | 39 | 40 | 41 | 42 |
|---|---|---|---|---|---|---|
| Process Parameters | | | | | | |
| Catalyst Type | M | M | M | N | N | N |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 11.75 | 10.70 | 10.60 | 13.92 | 13.73 | 14.13 |
| Ammonia/MEA mole ratio | 10.00 | 10.00 | 10.00 | 10.00 | 10.00 | 10.00 |
| Calculated Results | | | | | | |
| MEA conversion, % | 32.11 | 50.81 | 76.69 | 24.52 | 42.81 | 62.96 |
| EDA/PIP weight ratio | 11.86 | 7.84 | 3.02 | 14.76 | 7.29 | 3.42 |
| DETA/PIP weight ratio | 2.44 | 2.02 | 0.88 | 3.32 | 2.38 | 1.23 |
| AEEA/PIP weight ratio | 4.36 | 2.04 | 0.52 | 8.84 | 3.31 | 1.08 |
| Crude Product Composition, wt. % | | | | | | |
| EDA | 57.24 | 56.45 | 48.98 | 50.28 | 47.57 | 44.14 |
| PIP | 4.83 | 7.20 | 16.21 | 3.41 | 6.52 | 12.90 |
| DETA | 11.78 | 14.52 | 14.24 | 11.33 | 15.49 | 15.84 |
| AEEA | 21.03 | 14.70 | 8.38 | 30.10 | 21.59 | 13.93 |
| AEP | 1.14 | 1.17 | 2.91 | 0.99 | 1.23 | 2.41 |
| HEP | 0.25 | 0.37 | 0.83 | 0.16 | 0.34 | 0.71 |
| TETA | 1.86 | 3.01 | 3.91 | 1.86 | 4.19 | 5.50 |
| Others | 1.88 | 2.58 | 4.54 | 1.88 | 3.07 | 4.58 |

-continued

| Example No. | 43 | 44 | 45 | 46 | 47 | 48 |
|---|---|---|---|---|---|---|
| Process Parameters | | | | | | |
| Catalyst Type | O | O | O | P | P | P |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 11.10 | 11.43 | 11.79 | 12.93 | 12.80 | 12.45 |
| Ammonia/MEA mole ratio | 10.00 | 10.00 | 10.00 | 10.00 | 10.00 | 10.00 |
| Calculated Results | | | | | | |
| MEA conversion, % | 23.99 | 42.61 | 65.81 | 14.21 | 24.44 | 38.14 |
| EDA/PIP weight ratio | 11.93 | 8.89 | 3.89 | 19.88 | 14.96 | 8.00 |
| DETA/PIP weight ratio | 2.21 | 2.27 | 1.12 | 2.65 | 2.91 | 1.92 |
| AEEA/PIP weight ratio | 5.20 | 2.87 | 0.87 | 10.41 | 7.82 | 3.04 |
| Crude Product Composition, wt. % | | | | | | |
| EDA | 55.75 | 55.08 | 50.29 | 55.60 | 52.90 | 53.06 |
| PIP | 4.67 | 6.19 | 12.94 | 2.80 | 3.54 | 6.63 |
| DETA | 10.33 | 14.05 | 14.52 | 7.41 | 10.31 | 12.71 |
| AEEA | 24.30 | 17.77 | 11.23 | 29.11 | 27.66 | 20.18 |
| AEP | 1.40 | 1.17 | 2.28 | 1.44 | 1.15 | 1.34 |
| HEP | 0.26 | 0.32 | 0.70 | 0.00 | 0.27 | 0.56 |
| TETA | 1.52 | 2.96 | 3.89 | 0.62 | 1.66 | 2.74 |
| Others | 1.77 | 2.45 | 4.14 | 3.03 | 2.51 | 2.79 |

| Example No. | 49 | 50 | 51 | 52 | 53 | 54 |
|---|---|---|---|---|---|---|
| Process Parameters | | | | | | |
| Catalyst Type | Q | Q | Q | R | R | R |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 13.61 | 11.54 | 11.66 | 13.74 | 13.47 | 13.49 |
| Ammonia/MEA mole ratio | 10.00 | 10.00 | 10.00 | 10.00 | 10.00 | 10.00 |
| Calculated Results | | | | | | |
| MEA conversion, % | 23.21 | 37.25 | 59.34 | 25.82 | 42.63 | 64.70 |
| EDA/PIP weight ratio | 11.30 | 8.24 | 3.07 | 12.51 | 7.07 | 3.12 |
| DETA/PIP weight ratio | 2.10 | 1.89 | 0.76 | 2.50 | 1.80 | 0.90 |
| AEEA/PIP weight ratio | 4.22 | 2.58 | 0.57 | 5.69 | 2.28 | 0.72 |
| Crude Product Composition, wt. % | | | | | | |
| EDA | 57.30 | 55.86 | 50.45 | 54.07 | 53.51 | 47.54 |
| PIP | 5.07 | 6.78 | 16.44 | 4.32 | 7.57 | 15.25 |
| DETA | 10.66 | 12.82 | 12.51 | 10.82 | 13.63 | 13.67 |
| AEEA | 21.42 | 17.48 | 9.43 | 24.60 | 17.24 | 11.02 |
| AEP | 1.52 | 1.38 | 3.01 | 1.22 | 1.45 | 2.96 |
| HEP | 0.34 | 0.49 | 1.02 | 0.26 | 0.50 | 0.97 |
| TETA | 1.67 | 2.75 | 3.17 | 1.92 | 3.15 | 3.39 |
| Others | 2.01 | 2.44 | 3.97 | 2.79 | 2.95 | 4.67 |

| Example No. | 55 | 56 | 57 | 58 | 59 | 60 |
|---|---|---|---|---|---|---|
| Process Parameters | | | | | | |
| Catalyst Type | S | S | S | T | T | T |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 11.16 | 11.05 | 10.24 | 12.38 | 11.75 | 12.16 |
| Ammonia/MEA mole ratio | 10.00 | 10.00 | 10.00 | 10.00 | 10.00 | 10.00 |
| Calculated Results | | | | | | |
| MEA conversion, % | 24.31 | 39.74 | 61.35 | 31.55 | 47.90 | 66.54 |
| EDA/PIP weight ratio | 11.18 | 8.98 | 4.38 | 6.07 | 4.87 | 2.61 |
| DETA/PIP weight ratio | 2.02 | 2.04 | 1.13 | 1.53 | 1.54 | 0.79 |
| AEEA/PIP weight ratio | 5.07 | 2.98 | 0.95 | 2.85 | 1.50 | 0.45 |
| Crude Product Composition, wt. % | | | | | | |
| EDA | 55.00 | 56.00 | 52.90 | 48.64 | 48.94 | 45.70 |
| PIP | 4.92 | 6.23 | 12.08 | 8.01 | 10.06 | 17.52 |
| DETA | 9.94 | 12.73 | 13.64 | 12.26 | 15.52 | 13.79 |
| AEEA | 24.93 | 18.55 | 11.47 | 22.83 | 15.05 | 7.88 |
| AEP | 1.13 | 1.06 | 2.07 | 1.11 | 1.45 | 3.80 |
| HEP | 0.30 | 0.38 | 0.80 | 0.42 | 0.56 | 0.96 |
| TETA | 1.61 | 2.65 | 3.34 | 2.97 | 4.74 | 4.64 |
| Others | 2.17 | 2.39 | 3.70 | 3.75 | 3.68 | 5.70 |

-continued

| Example No. | 61 | 62 | 63 | 64 | 65 | 66 |
|---|---|---|---|---|---|---|
| Process Parameters | | | | | | |
| Catalyst Type | U | U | U | V | V | V |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 12.60 | 11.06 | 10.68 | 12.19 | 12.36 | 11.99 |
| Ammonia/MEA mole ratio | 10.00 | 10.00 | 10.00 | 10.00 | 10.00 | 10.00 |
| Calculated Results | | | | | | |
| MEA conversion, % | 27.14 | 45.68 | 67.23 | 25.15 | 39.94 | 58.24 |
| EDA/PIP weight ratio | 5.51 | 3.63 | 2.27 | 14.67 | 9.75 | 4.93 |
| DETA/PIP weight ratio | 1.38 | 1.26 | 0.77 | 1.82 | 1.50 | 0.88 |
| AEEA/PIP weight ratio | 3.81 | 2.32 | 0.65 | 2.25 | 1.26 | 0.52 |
| Crude Product Composition, wt. % | | | | | | |
| EDA | 43.12 | 38.84 | 40.65 | 72.24 | 69.04 | 62.70 |
| PIP | 7.83 | 10.71 | 17.91 | 4.93 | 7.08 | 12.72 |
| DETA | 10.77 | 13.48 | 13.78 | 8.97 | 10.61 | 11.23 |
| AEEA | 29.85 | 24.33 | 11.62 | 11.07 | 8.91 | 6.59 |
| AEP | 1.76 | 1.64 | 3.45 | 0.97 | 1.33 | 2.23 |
| HEP | 0.44 | 0.72 | 1.24 | 0.22 | 0.35 | 0.52 |
| TETA | 2.45 | 4.51 | 4.79 | 0.82 | 1.28 | 1.73 |
| Others | 3.79 | 5.28 | 6.56 | 0.79 | 1.39 | 2.27 |

Table III shows the effectiveness of various ratios of nickel:rhenium promoters (magnesium, zinc, and potassium) on the preferred gamma/theta alumina carriers of the present invention. Catalyst V was prepared using a preferred nickel:rhenium:boron catalyst formulation, U.S. Pat. Nos. 4,123,462 and 5,068,329, on a preferred gamma/theta alumina of the present invention, as a comparative example.

What is claimed is:

1. A reductive amination process comprising reacting MEA in the presence of ammonia, hydrogen and a reductive amination catalyst comprising at least one catalytically effective reductive amination metal incorporated with a transitional alumina carrier, thereby yielding a product mix having increased aminoethylethanolamine levels relative to piperazine.

2. The process of claim 1 wherein the catalytically effective reductive amination metal is selected from the group consisting of nickel, rhenium, cobalt, rhodium, iridium ruthenium, palladium and platinum.

3. The process of claim 1 wherein the transitional alumina carrier is selected from the group consisting of delta, theta, gamma/theta, delta/theta, theta/alpha phases and mixtures thereof.

4. The process of claim 1 wherein the reductive amination catalyst further comprises a metal or oxide promoter which is an element selected from the group consisting of Group IA, Group IIA, and Group IIB elements of the Periodic Table.

5. The process of claim 4 wherein the promoter is magnesium, zinc or mixtures thereof.

* * * * *